United States Patent [19]

Haast

[11] 4,341,762

[45] Jul. 27, 1982

[54] USE OF SNAKE VENOMS FOR TREATMENT OF NEUROLOGICAL AND RELATED DISORDERS

[76] Inventor: William E. Haast, 12655 S. Dixie Hwy., Miami, Fla. 33156

[21] Appl. No.: 251,745

[22] Filed: Apr. 7, 1981

[51] Int. Cl.³ ....................... A61K 39/00; A61K 35/58

[52] U.S. Cl. ........................................ 424/88; 424/98

[58] Field of Search .................................... 424/98, 88

[56] References Cited

U.S. PATENT DOCUMENTS 4,012,502 3/1977 Philpot .................................. 424/98

4,126,676 11/1978 Sanders ................................ 424/98

OTHER PUBLICATIONS

Okonogi et al.-Chem. Abst. vol. 92 (1980) p. 135, 396d.

*Primary Examiner*—Sam Rosen

*Attorney, Agent, or Firm*—Kenneth E. Darnell

[57] ABSTRACT

The present invention provides stable compositions of matter including venoms and/or venom fractions extracted from various elapid and viperid snakes, the present compositions of matter having pharmacological activity and being further useful in treating the symptoms of neurological and other disorders, particularly disorders which are caused by malfunction of the immune mechanisms. The present compositions of matter generally include a post-synaptic component capable of binding to nicotinic acetylcholine receptors of cells, a pre-synaptic component capable of inhibition of acetylcholine release, and a viperid component considered to be stimulative of the immune system. Methods of preparation and use of the present compositions of matter are also disclosed.

40 Claims, No Drawings

USE OF SNAKE VENOMS FOR TREATMENT OF NEUROLOGICAL AND RELATED DISORDERS

BACKGROUND OF THE INVENTION

1. Field of the Invention

The invention relates generally to compositions of matter and methods for use thereof in the treatment of the symptomology of disease syndromes involving the neurological system of the body, particularly chronic degenerative neurological diseases.

2. Description of the Prior Art

The recognition of the intense biological activities of snake venoms came early to man, this recognition being soon followed by attempts to utilize such venoms in the treatment of varying physical afflictions. Early practitioners of homeopathic medicine made snake venoms an integral part of the pharmacopeia of the times, a practice still continued today in certain cultures. Unfortunately, virtually none of these essentially homeopathic traditions have stood the dual test of time and of subjection to modern concepts of efficacy. However, the recognition of the extraordinary bioactivity of snake venoms has remained and, within the recent past, has finally resulted in increased understanding of the venoms and of their utility. In particular, intensive research in this century has revealed that snake venoms consist of a variety of proteinaceous and other components which have great utility in the research laboratory for study of biological systems. Certain snake venom components or "fractions" have also been proven therapeutically effective as anticoagulants, pain relievers, etc. Pharmaceutical preparations containing snake venom fractions are now available commercially and have proven to be effective.

Exemplary of recent developments in the utilization of snake venoms for treatment of the human body is the enzyme isolated by Reid et al from Agkistrodon rhodostoma venom disclosed in U.S. Pat. No. 3,657,416, the patent also disclosing a method for therapeutic treatment of the human body with the enzyme. In U.S. Pat. No. 3,888,977 to Sanders, a treatment of neurological diseases afflicting humans, particularly amyotropic lateral sclerosis, is taught using detoxified snake venoms including a modified neurotoxin derived from the Bungarus genus. Sanders further teaches in U.S. Pat. No. 4,126,676 similar methods for treatment of neurological disorders using modified neurotoxins derived solely from the Naja genus. The Sanders patents teach that these ophidian venoms must be detoxified in order to allow the introduction of an effective dosage into the body. As is recognized in the patents, detoxification of the venoms thus used risks destruction of the activities of the venoms which are being sought to effect the intended treatment. The present invention utilizes various combinations of snake venoms and snake venom fractions which retain full bioactivity by virtue of not having been subjected to detoxification processes. The biologically active compositions of matter thus provided according to the invention are herein disclosed as having exceptional utility in the treatment of the symptomatic effects of neurological and other disorders, certain of which disorders are potentially of viral and/or autoimmune origin.

SUMMARY OF THE INVENTION

The present invention provides pharmacologically active compositions of matter comprised of snake venoms and/or snake venom fractions and methods for use of the compositions of matter in the treatment of particular disorders and classes of disorders which afflict man. The present compositions of matter are administered in disease mitigating quantities into the systemic circulation preferably by subcutaneous, intramuscular or intravenous injections. In addition to treatment of the symptomology of progressive degenerative neurological disorders, such as multiple sclerosis and amyotropic lateral sclerosis, the present invention provides compositions of matter useful for treatment of the disease complex generally referred to as arthritis, particularly rheumatoid arthritis. According to teachings herein made, the present invention further envisions the treatment of viral and autoimmune disorders by stimulation of the immune mechanisms of the body.

In a preferred embodiment, the invention provides compositions of matter comprised of a neurotoxin having postsynaptic activity and which binds strongly to receptor sites of cells, reversibility of the binding being preferred. Suitable post-synaptic neurotoxins are found in reptile venoms of the family Elapidae, subfamily Elapinae, and particularly the genera Naja, Ophiophagus, Dendroaspis, and others. The well-known "long" post-synaptic neurotoxin, known as $\alpha$-toxin or as cobratoxin, of *Naja naja siamensis* (kaouthia) is particularly suited as the post-synaptic neurotoxin or receptor site "blocking agent" of the invention.

The present compositions of matter also preferably include a pre-synaptic neurotoxin of the type which typically inhibits the release of acetylcholine and which are generally regarded as having "phospholipase activity", the pre-synaptic neurotoxins of choice also being relatively reversible. The pre-synaptic neurotoxins of *Bungarus multicinctus,* Family Elapidae, subfamily Elapinae, are preferred, these neurotoxins collectively being referred to as $\beta$-Bungarotoxin. Similar pre-synaptic neurotoxins include Taipoxin from *Oxyuranus scutellatus,* Notexin from *Notechis scutatus,* and Crotoxin from *Crotalus durissus terrificus.*

The present compositions of matter preferably are provided also with a further component comprising a venom having the capability of stimulating the immune mechanisms of the body. This stimulation is considered to include both the cell-mediated immune system and the interferon system, these systems being considered to be simultaneously operative in mammals. Preferred choices for this third component of the present composition of matter include venoms of the Family Viperidae, and particularly the several genera of the subfamily Crotalinae. Due to the availability and suitable activity, venom of *Agkistrodon piscivorus* is typically used.

The present composition of matter can include the whole venom of the particular venom from which a particular activity is being sought or only a particular fraction or fractions from the venom. As an example, a whole venom of a Bungarus species can be included in the present composition of matter with the particular intent of imparting the activity of the pre-synaptic neurotoxins to the compositions of matter. Inclusion of the whole venom will also introduce a post-synaptic neurotoxin from the "pre-synaptic source", which post-synaptic neurotoxin can potentially complement the post-synaptic neurotoxin present in the compositions of matter from the other elapid venom source specifically intended to contain post-synaptic activity. Conversely, a whole venom such as from the Naja species mentioned above will typically contain pre-synaptic neurotoxins which can potentially complement the pre-synaptic activity of the "Bungarus" component of the mixture. However, it is preferred to fractionate the two "elapid" venoms, that is, the venoms useful for post-synaptic and pre-synaptic activities, to isolate these activities from the whole venoms prior to a mixture of the isolated fractions to form the compositions of the invention.

The viperid component of the invention is preferably utilized as a whole venom since these venoms contain a number of differing substances, enzymatic in nature and otherwise, which are seen to stimulate the immune mechanisms of the body. The various physiologically active compounds present in these venoms, as well as the "elapid" venoms and/or fractions comprising the components of the present invention noted above, are also seen to liberate or stimulate the production of pharmacologically active substances in the body, certain of these substances being operative within present concepts of the immune systems of the body.

As will be described in greater detail hereinafter, the present compositions of matter are seen to stimulate the immune mechanisms of the body. The present compositions of matter are particularly seen to stimulate the production of the substance known as "interferon" or a precursor thereto, this stimulation occurring due to the projected presence of proteins having at least portions which resemble double-standard RNA molecular structures or which contain enzymatic activities capable of converting precursor proteins to interferon stimulating or activating agents. Stimulation of that portion of the body's immune system which involves interferon or the complex activity within the body attributed to interferon causes the present compositions of matter to be useful further as antiviral and as antiautoimmune agents. Evidence exists in the treatment of neurological disorders that the present compositions of matter exhibit antiviral capability. Evidence also exists that the present compositions of matter find utility for treatment of autoimmune disorders, such disorders being generally defined as involving a false recognition of certain body cells as "foreign" and, through cell-mediated immune response, subsequent "attack" of the supposedly foreign body. Such pathologies are generally considered to be complement-mediated and, through stimulation of the interferon immune system, can be treated according to the present invention.

With the production of interferon thus stimulated, binding of the interferon or by other substances caused to be produced by interferon to cellular membrane receptor sites occurs to thereby form a "shield" against cellular assault such as is now believed to occur with disorders of viral origin and complement-mediated pathologies.

In addition to the stimulation of the immune system as indicated above, the present compositions of matter are seen to contain neurotoxins which bind to nerve cell receptor sites and thus to act as "blocking agents" on binding to the sites. The normal functioning of these cell receptor sites apparently are disrupted by the various disease syndromes for which the present compositions of matter find utility, a blocking by the neurotoxins acting to prevent or ameliorate the deleterious affects which occur as usual results of the disorders.

Accordingly, it is a primary object of the invention to provide compositions of matter having pharmacological activity and which comprise mixtures of whole venoms and/or venom fractions, particularly venoms of the elapid and viperid snakes.

It is another object of the invention to provide physiologically active compositions of matter comprised of post-synaptic and pre-synaptic neurotoxins, preferably reversible neurotoxins and preferably isolated from elapid snakes such as species of the Naja and related genera for the post-synaptic neurotoxin and such as species of the Bungarus genus for the pre-synaptic neurotoxin, a viperid venom and particular a Crotalid venom being also a part of the mixtures.

Yet another object of the invention is to provide compositions of matter as noted herein which are useful for the treatment of the symptomology of disease syndromes including degenerative neurological diseases such as multiple sclerosis and amyotropic lateral sclerosis, for treatment of disorders of a viral nature as well as for treatment of disorders which may be at least partially autoimmune in origin.

It is a further object of the invention to provide methods of treatment using the compositions of matter noted herein for treatment of the symptomology of the disease complex referred to as arthritis and particularly including rheumatoid arthritis.

Further objects and advantages of the invention will become more readily apparent in light of the following detailed description of the preferred embodiments of the invention.

DESCRIPTION OF THE PREFERRED EMBODIMENTS

In preferred embodiments, the invention comprises a mixture of venoms and/or venom fractions having particular characteristics and being contained in normal saline solution preserved with thimerosal, the mixtures being preferably injected into the body as a sterile, pyrogen-free solution. The mixtures of the invention exhibit definite pharmacological activity and are useful in mammals for treatment of the symptomology of various disease syndromes as described herein. As a definite pharmacological activity, the present mixtures increase the titer of antibodies in the blood to the venoms and/or venom fractions contained in the mixtures, thereby developing an increased immune resistance thereto.

In general, the present mixtures include at least one post-synaptic neurotoxin such as is usually referred to as a curaremimetic post-synaptic neurotoxin and which has an activity described as involving binding to nicotinic acetylcholine receptors of cells. A large number of known neurotoxins which can be isolated from snake venoms, particular from the elapid snakes, have post-synaptic activity. While the scope of the invention includes all such neurotoxins, the invention is preferably practiced through use of a post-synaptic component which is relatively reversible in its binding to the receptor site. Accordingly, the α-toxin or toxins, also known as cobratoxin, isolated from the venom of the elapid Naja naja siamensis (kaouthia) is preferred both due to the exhibited degree of reversibility and due to availability. This neurotoxin is generally referred to as a "long" neurotoxin. For this reason, the post-synaptic component of the present mixtures is also referred to hereinafter as the "cobra" component. Other venoms containing post-synaptic neurotoxins useful as the cobra component include particularly venoms extracted from snakes of the Family Elapidae, subfamily Elapinae, and various genera preferably comprising Naja, Ophiophagus, Dendroaspis, Hemachatus, Micrurus, Micrurodies, Calliophus, and Leptomicrurus. The α-toxins of the Hydrophiidae also have a post-synaptic neurotoxin which is seen to be useful as the cobra component of the present mixtures. While the Bungarus genus also produces post-synaptic toxins, the use of the α-toxins of the species of this genus, particularly Bungarus multicinctus, is least preferred since these post-synaptic neurotoxins are relatively less reversible. It is also to be understood that whole venoms of one of the above-noted species can be used in the formulation of the present mixtures, the use of whole venom also introducing other pharmacologically active substances into the mixtures. Certain of these substances, such as nerve growth factor and the like, can make important, though not presently completely understood, contributions to the treatment of disease syndromes for which the present mixtures are useful.

The present mixtures also preferably include a component having pre-synaptic activity, which activity is normally defined as inhibiting the release of acetylcholine. These pre-synaptic neurotoxins typically exhibit a phospholipase structure and may be complexes of two or more molecular subunits. As with the "cobra" component of the present mixtures, a relatively high degree of reversibility of the pre-synaptic component is preferred. The several pre-synaptic neurotoxins which can be isolated from venom extracted from the elapid Bungarus multicinctus and which are known generally as β-bungarotoxin are preferred for use as the pre-synaptic component. Accordingly, the pre-synaptic component of the present mixtures is also referred to hereinafter as the "krait" component. Other venoms useful as the pre-synaptic neurotoxin include those venoms extracted from snakes of the Family Elapidae, subfamily Elapinae, and various genera preferably including Bungarus, Oxyuranus and Notechis. In particular, Taipoxin, a toxin which can be isolated from the venom of Oxyuranus scutellatus and Notexin, isolated from the venom of Notechis scutatus, exhibit pre-synaptic activity. Crotoxin, a material isolated from the venom of a viperid snake, Crotalus durissus terrificus, also exhibits a pre-synaptic activity which is seen to be useful according to the invention. While the Hydrophiidae, and particularly the Laticaudinae, genus Laticauda, would be considered to have a pre-synaptically active component due to the close taxonomic relationship of these snakes to the kraits, no fraction of these venoms having pre-syanptic activity have apparently been isolated. It is thus not possible to state with certainty that the use of the hydrophid venoms would be useful to the practice of the invention as a contributor of a pre-synaptic component. However, it is believed that the hydrophid venoms would also be useful. It is also to be understood that whole venoms of the above-noted species can be used in the formulation of the present mixtures as the "krait" component in a manner similar to the use of whole venoms as the "cobra" component. In such situations, other pharmacologically active substances, and particularly post-synaptic toxins present in the "krait" component can complement or replace the post-synaptic toxins of the "cobra" component.

A third preferred component of the present mixtures is best referred to as the "viper" component and preferably comprises the whole venom extracted from at least one species of the various subfamilies of the Family Viperidae, particularly the subfamilies Viperinae and Crotalinae. The Crotalinae are preferred and particularly include the genera Agkistrodon, Bothrops, Crotalus, Lachesis, Sistrurus, and Trimeresurus. The "viper" component is particularly intended to stimulate the immune mechanisms of the body. Enzymatic and other components of the viperid venoms useful according to the invention are seen to either stimulate the immune systems directly or to stimulate production of pharmacologically active substances such as interferon or precursors thereto. Stimulation of the body's immune systems is seen to have particular significance in the treatment of diseases which are viral or autoimmune in nature, the symptomology of diseases as apparently widely varying as rheumatoid arthritis and multiple sclerosis being treated according to the invention due likely to having generally similar causes. It is to be noted that the cobra and krait components of the present mixtures also stimulate the immune systems of the body in addition to that stimulation intended for the viper component. The species Agkistrodon piscivorus is generally used in formulation of the present mixtures due to demonstrated efficacy and availability.

The publication entitled *Snake Venoms,* Volume 52 of the Handbook of Experimental Pharmacology, Springer-Verlag, New York, 1979, and edited by Chen-Yuen Lee, contains particularly taxonomic groupings of the snakes referred to herein, the classifications so provided being generally followed herein except as to the general grouping of the sea snakes into a single family, the Hydrophiidi. This publication is incorporated hereinto in its entirety. The present mixtures are useful as being pharmacologically active compositions of matter which find particular utility in the treatment of the symptomology of progressive degenerative neurological diseases in mammals including man and including but not being limited to multiple sclerosis, amyotropic lateral sclerosis, muscular distrophy, Parkinson's disease, myasthenia gravis, kuru, meningitides, retinitis pigmentosa, and herpes erythermatosis inter alia. Such diseases are typically of motor cell origins to neuromuscular junction, axones and nerve myelin sheaths, the treatment comprising the administration by injection of a disease mitigating quantity of the present mixtures. The symptomology of the disease complex generally referred to as arthritis and particularly rheumatoid arthritis can also be treated according to the invention. Further, diseases of known viral origin and potential viral origin can also be treated according to the invention. Due to stimulation of the immune systems of the body, treatment of autoimmune disorders is also contemplated according to the invention.

As at least partial explanation of the efficacy of the present composition of matter, it is to be noted that one presently considered cause of degenerative neurological diseases is from specific infection such as viral infection or the invasion by proteins which have deleterious affects on the cells. In such situations, the symptomology of the disorder is caused by the action of the virus or protein on nerve cell receptors. Whether or not nerve cell receptors are discrete anatomical structures or merely the theoretical embodiment of cellular activities, nerve cells are known to function as if physical receptors do exist. The neurotropic character of at least certain of the components of the present mixtures causes blockage of the nerve cell receptors, thereby preventing or alleviating the noxious effects of an invading pathogenic bacteria, virus or protein. An excellent summary of the pharmacology of muscular transmission is to be found on pages 319–321 of *Snake Venoms,* supra, which is incorporated hereinto by reference.

The reversible post-synaptic nerve receptor inhibitors provided to the present mixtures at least as the "cobra" component are thus seen to act as cell-specific blocking agents. By alteration of the cell due to binding of the neurotoxins to cell receptor sites or simply by making the sites unavailable, an invading or slow-acting virus or protein is prevented from causing at least some of the symptoms associated with such disorders.

Degenerative neurological diseases may also originate in whole or in part as inflammatory processes involving the immune mechanisms of the body, it being noted that multiple sclerosis patients, for example, have a lowered immunological response. Disorders such as multiple sclerosis can be seen to at least partially involve a mechanism which is autoimmune in origin. Stimulation of the body's immune mechanisms by the present mixtures thus potentially increases the body's own ability to counteract the causative factors of such disease syndromes. The components of the present mixtures and particularly the viper component is seen to include a variety of enzymes and proteins which stimulate the liberation of pharmacologically active substances. The presence in the present mixtures of natural inducers in vivo of interferon or interferon-like substances and/or precursors is seen to cause the body to produce interferon in essentially the same manner as occurs when the body is challenged by viral agents or by synthetic double-stranded RNA molecules, such as poly rI:rC, a synthetic RNA consisting of paired strands of riboinosinic acid and ribocytidylic acid, in vivo, hydrolyzable derivatives of which are disclosed by T'so et al in U.S. Pat. No. 4,024,222. The interferon thus induced is seen to be essentially indentical in activity to that proteinaceous material or activity described by Isaacs and Lindenmann in U.S. Pat. No. 3,699,222, the interferon thus induced having antiviral, antibacterial, and other capabilities.

The disease complex referred to as cancer, particularly those cancers apparently caused by viral carcinogens, can also be seen to be caused or exacerbated by a reduction or failure in the interferon immune system of the body, the converse being that viral carcinogens which normally are present in the body or which attack the body from time to time are substantially countered by the normal functioning of the interferon system. A cessation or impairment in function of the body's interferon immune system would thus cause increased susceptibility to viral agents including viral carcinogens and a resulting infection to include under certain circumstances the development of certain of the foregoing disease syndromes including cancer pathology. The binding of interferon induced in vivo according to the invention to cellular membrane receptor sites to form a "shield" against cellular assault thereby results in relief of at least certain symptomatic aspects of a particular disorder. Enzymatic venom proteins, such as ritonuclease and/or deoxyribonuclease inter alia, acting on cellular nucleotides likely constitute mechanisms for production of double-stranded RNA molecular structures which then act to induce the production of interferon in vivo.

The thus described induction of interferon either directly or indirectly according to the invention allows also for at least one mechanism for the treatment of autoimmune disorders, the pathology of such disorders typically being complement-mediated and occurring as a result of the malfunctioning of the cell-mediated immune response system as noted above. Diabetic patients being treated for multiple sclerosis with the present compositions of matter have reduced or eliminated their need for insulin. Since diabetes can be considered to have elements of autoimmune pathology, it is believed that the induction of interferon according to one mechanism of action of the invention acts to relieve the symptomology of at least certain autoimmune disorders.

As noted above, the present compositions of matter are useful in treatment of the symptomology of the disease complex commonly referred to as arthritis and particularly rheumatoid arthritis. This disease symptomology involves localized inflammation of joint tissue inter alia, the causative factors thereof being now believed to contribute or include malfunction of the immune mechanisms essentially of the nature of an autoimmune condition. The stimulation of the body's immune mechanisms as noted above relative to the discussion of degenerative neurological disorders is believed to constitute a major factor in the symptomatic relief of arthritis brought about by practice of the invention. Whether inferon induction be operative, the complex combination of proteins and enzymes present in the compositions of matter of the invention are seen to trigger at least a temporary restoration of the body's immune mechanisms to normal functions. Evidentiary thereto, patients who have received cortisone therapy for an appreciable period do not immediately respond favorably to treatment according to the present invention. Little or no normal inflammatory response at the site of injection is noted in such patients during a several week period of weaning from steroid therapy. Those patients who thus do not experience local inflammatory reaction following injection exhibit a corresponding delay in their response to the present treatment. It is accordingly believed that the immune system thus impaired or suppressed by prior steroid therapy is not as readily stimulated by the present therapy, this reaction being thus indicative of the involvement of the immune system in the therapeutic functioning of the invention. As a result of these considerations, the complement inhibitor known as anticomplementary protein or as cobra venom factor is preferably removed from the typical "cobra" component of the present mixtures and, if present to an appreciable degree, from other components thereof in order that the immune mechanisms of the body not be suppressed.

Treatment of arthritis according to the invention is also believed to be at least partially due to the interferon mechanism discussed above relative to the treatment of degenerative neurological disorders. The efficacy of the present invention relative to viral agents such as herpes zoster, herpes simplex and the reduction or loss of virally induced moles and warts strongly indicates the operation of such a mechanism which is at least temporarily interferon-like in nature.

The potential presence of nerve growth factors in the venoms comprising the present compositions of matter, either in the elapid or viperid venoms, is believed to contribute to symptomatic relief, particularly in patients suffering from degenerative neurological disorders such as multiple sclerosis, by direct stimulation of the nerves per se and the possible inducement of regeneration of nerve matter.

The pre-synaptic components, that is, the krait components of the present mixtures, are also seen to improve nerve conduction, at least one of the toxins comprising β-bungarotoxin being known to illicit a hypersensitive sensory nerve response, the impaired nerve cell thus being directly stimulated. This pre-synaptic activity of the mixtures is considered to be responsible for improved atonic bladder control, increased sensitivity to feeling in the extremities, greater strength and increased endurance particularly to patients suffering from multiple sclerosis. The ability of some non-ambulatory patients to become ambulatory is likely to result from symptomatic relief due to improved nerve conduction induced by the krait component. Nerve growth factor present in the mixtures or the action of the mixtures on the disease processes per se may also contribute to such recovery, particularly for patients who demonstrate a gradual, continuing recovery of mobility.

In summary, the invention provides for treatment of the symptoms of diseases of viral origin including poliomyletis, herpes simplex, herpes zoster, herpes genitalis inter alia and diseases of suspected viral origins such as multiple sclerosis and amyotropic lateral sclerosis where the mechanisms are seen to be complex in nature and which likely involve more than one mechanism. Diseases of the immune system such as multiple sclerosis, par planitis, and the conditions relating to the arthritis complex are also subject to symptomatic treatment according to the invention. Degenerative neurological disorders such as are described herein are further subject to treatment according to the invention.

A preferred protocol for the preparation of the present compositions of matter initially involve the collection of raw venom from the particular species of snakes referred to above, raw venom production being by known methodology. Venom is collected in all instances from healthy animals of known species origin. After venom collection with all species, the raw liquid venom is centrifuged at approximately 2000 rpm for at least 2 minutes, the liquid venom thus separated from cellular debris being frozen and then lyophilized according to known procedures. The lyophilized venom from serial extractions is pooled into batch lots and stored at −15° C. Once sufficient venom quantities are accumulated, the accumulated quantity is reconstituted in a ratio of 1 g of lyophilized venom to 5 ml of 18 megohm water. The reconstituted venom is then centrifuged at approximately 12,000 rpm (20,000×G) at 0° C. for 30 minutes. The resulting clear supernatant is withdrawn and frozen prior to lyophilization to produce a dry powder which is stored at −15° C. The lyophilized venom thus produced is designated by species and referred to as raw material of the species. Each venom species is thus produced, it being possible to avoid the first lyophilization step in the event that sufficient animals are available to produce large quantities of venom at a given time.

The krait component of the present mixtures, which is preferably prepared from Bungarus multicinctus, is column fractionated using SP-Sephadex C-25 using a starting buffer of 0.1 M sodium acetate at pH 5.0 and containing 0.005% Thimerosal and a terminating buffer of 0.1 sodium acetate, pH 5.0, and containing 0.6 M sodium chloride and 0.005% Thimerosal. Preparation of the Sephadex column is accomplished by suspension of 25 g of SP-Sephadex C-25 in one liter of 18 megohm later followed by boiling for 2 hours. After cooling and settling of the gelled particles, the supernatant is removed by decantation and the SP-Sephadex is washed twice more with water. Subsequently, the SP-Sephadex is resuspended and washed with the initial buffer and the slurry packed into a Pharmacia K50/30 (5×30 cm) chromatography column water-jacketed at 5° C. using a Colora circulating cooler. After packing, the column is washed with at least two column volumes of the initial buffer at a flow rate of approximately 100 ml/hr. A quantity of 0.5 g of the raw material consisting of the krait component (preferably Bungarus multicinctus) prepared as indicated above is dissolved in approximately 2.5 ml of the starting buffer and pumped onto the column at 10 ml/hr. The column is then eluted with the starting buffer at 50 ml/hr until a total volume of 200 ml is collected, at which time the gradient elution is begun. Gradient elution is accomplished by using 2500 ml of the terminating buffer with the aid of an LKB 11300 Ultrograd gradient mixer, the gradient being linear. The effluent is monitored at 280 nm using an LKB 2138 Uvicord S or Uvicord II. The β-bungarotoxin complex appears at approximately 1500 ml and extends to 2650 ml. The β-bungarotoxin complex fraction, approximately 1150 ml, are placed into an ultrafiltration cell (Millipore no. XX42 142 50) equipped with an ultrafiltration filter (Millipore PSAC 142 50) having a 1000 nominal molecular weight cutoff. The volume is reduced to approximately 50 ml. Nitrogen pressure on the cell is 50 psi. Approximately 500 ml of 18 megohm water is introduced into the cell and the amount is again reduced to approximately 50 ml, this process being repeated and the final retentate being withdrawn from the cell and delivered into clean lyophilized flasks for freezing. The frozen retentate is then lyophilized by connecting the flask to an automatic freeze dryer, Virtis Model No. 10-010 in a known manner. The lyophilized material is designated "krait bulk powder" and is stored at −15° C.

Centrifuged and lyophilized venom constituting the raw material for the cobra component of the present mixtures is produced according to the procedures outlined above. The lyophilized raw material for the cobra component is column fractionated using Sephadex G-50, the buffer being 0.1 M sodium acetate, pH 5.2, containing 0.005% Thimerosal. To prepare the column, multiples of 25 g of Sephadex G-50 Superfine are suspended in multiples of one liter units of 18 megohm water and then boiled for 2 hours. After cooling and settling of the gelled articles, the supernatant is removed by decantation and the Sephadex is washed twice more by resuspension and settling using water. Subsequently, the Sephadex is suspended in buffer and the slurry packed into a Pharmacia K100/100 (10×100 cm) chromatography column water-jacketed at 5° C. using a Colora recirculating cooler. After packing the column, it is washed with at least two column volumes of the same buffer at a low rate of 200 ml/hr. A 4.5 quantity of the raw material preferably consisting of the lyophilized venom of *Naja naja siamensis* (kaouthia) is dissolved in 22.5 ml of buffer and pumped in ascending direction onto the column at the rate of 7.5 ml/hr. The column is then eluted with buffer at the rate of 2.5 ml/$cm^2$/hr, the effluent being monitored at 280 nm using an LKB2138 Uvicord S or Uvicord II. Three groups of fractions are eluted from the column, fraction A corresponding to the void volume of the column and containing cobra venom factor, L-amino acid oxidase and other large molecular weight non-toxic fractions; fraction B corresponding to the toxic fraction eluting after the void volume and proceeding the low molecular weight peptides of fraction C; and, fraction C is the inclusion volume of the column and containing low molecular weight peptides. A pooling of the B fractions (approximately 3180 ml) is placed into an ultrafiltration cell and filtered in the same manner as is described relative to production of the krait component. The lyophilized retentate is stored at −15° C. and is designated "(cobra bulk powder)", approximately 40–50% of the lyophilized cobra venom being recovered as the cobra bulk powder.

The "cobra bulk powder" essentially comprises post-synaptic neurotoxins or α-toxins while the "krait bulk powder" essentially comprises pre-synaptic neurotoxins or β-toxins.

The viper component of the present mixtures is prepared by collection, centrifugation and subsequent pooling and lyophilization of raw venom extracted from the candidate viperid snakes, particularly Crotalid snakes which preferably comprises Agkistrodon piscivorus according to procedures indicated hereinabove. The lyophilized pool of venom is stored as a dry bulk powder at −15° C. and is designated as "viper bulk powder", the viperid component of the present mixtures not being subjected to fractionation.

While the ratios of the various bulk powders can vary as will be indicated hereinafter and while the dilution thereof within the solution intended for administration can also vary, a typical mixture is formed by mixture of a first solution comprising 0.88 g of Thimerosal in 2.0 l of injectable saline. A second solution is prepared using 0.176 g each of the krait bulk powder and of the cobra bulk powder with 1.76 g of the viper bulk powder mixed in 2.0 l of injectable saline. The first and second solutions are mixed and passed through a prefilter, the prefilter being washed with two 1.0 liter washes of injectable saline. Approximately 2.8 l of injectable saline is then added to the resulting solution to produce a quantity of bulk solution sufficient to comprise 8.8 liters. The bulk solution thus produced is passed through a sterile filter and then packaged. The prefiltration step is preferably accomplished through a Millipore filter stack consisting of a prefilter (AW06 142 50), a 0.45 micron (HAWP142 50) filter and a 0.22 micron (GSWP 142 50) filter. Sterile filtration is accomplished by filtration through a 0.22 micron filter in a known manner. Packaging of the resulting solution is performed in a sterile work area, preferably equipped with a horizontal laminar flow hood work station including HEPA filters. Packaging is accomplished according to known sterile packaging techniques. Standard pyrogen testing and toxicity testing ensures the safey of the solutions for injection into mammals, including man. The packaged product is stored between 2° and 8° C.

In use, the dosage of the composition is initiated at approximately 0.10 cc daily, preferably administered subcutaneously in the deltoid region of the upper arm, administration being made to alternate arms. After a 30-day period, patient response is evaluated and dosage modified accordingly. When increases are warranted, the dosage is changed step-wise in 0.10 cc increments. Dosages of greater than 1.0 cc of the solution prepared as indicated above can be administered over extended periods without deleterious effects. Once an effective dosage level is established, the regimen is continued indefinitely in the case of neurological diseases, but can be reduced to one or two injections per week for inflammatory disease states depending on demonstrated improvement. It is to be noted that the method of administration can be other than by the subcutaneous route and can be adjusted according to known considerations for weights of the individual receiving the injections. Depending upon individual considerations such as weight, the strength of the solution, and other factors, an effective dosage can be described in a clinical situation.

Since the present mixtures comprise proteinaceous materials, preliminary testing is accomplished to determine possible initial hypersensitivity. A quantity of 0.10 cc of a 1:10 dilution of a solution such as described above in normal saline is injected intradermally in the inner forearm. Hypersensitivity is demonstrated at the injection site within 24 hours. If a hypersensitive reaction is noted, a desensitization regimen is initiated according to known techniques prior to the initiation of therapy.

Other than the occasional adverse reaction which would be expected from hypersensitivity, no adverse systemic reactions are encountered with therapy administered according to the invention with the exception of occasional induration at the injection site usually accompanied by swelling, itching and mild pain. In some individuals, small vesicles occur at the injection site, these vesicles being more prominent in patients who have been subjected to extended steriod therapy. In some individuals, an apparent transient hypersensitivity of the teeth and jaw muscles occurs. These mild side effects are temporary and typically disappear within 72 hours. In patients with a history of hypertension, an anti-hypertensive reaction is noted and is considered to be a beneficial side effect. As with all materials administered to the body, care is used in the treatment of patients exhibiting coronary problems. Contraindications include pregnant women and individuals having a demonstrated history of allergic reaction except those who have been desensitized as indicated above. Individuals previously receiving steroid therapy should have this therapy gradually reduced as treatment according to the invention is initiated. Delayed improvement is typically expected in patients who have been subjected to steroid therapy for an extended period of time.

Literally thousands of case histories exist which relate to the treatment of the varying disease pathologies referred to herein. In the particular treatment of arthritis, patients treated in the State of Florida under the care of a licensed medical practitioner and who have been diagnosed as having arthritis, including rheumatoid arthritis, by medical practitioners licensed in various states, clearly show relief from certain symptomology of the arthritis disease complex. In particular, inflammation and pain are reduced and mobility is improved. The relief thus obtained is long term in nature and continues even after termination of the course of treatment, thereby indicating an activity of the present invention on the inflammatory process per se. In treatment of arthritis, those patients who develop an immediate local reaction in the form of induration, swelling and pain, appear to respond most favorably and most rapidly, a direct correlation appears to exist between patients who do not experience any local inflammatory reaction following injections and a delayed response to the injections. This correlation is noted almost entirely in patients who have received cortisone therapy for appreciable periods prior to treatment according to the present invention. It is believed that the action of the body's immunological systems has been suppressed or impaired by the steroid treatment, thereby lessening the ability of the present mixtures to stimulate the body's immune systems until the patient can be weaned from steroid therapy. Particular case histories involving the treatment of the arthritis disease complex are given hereinafter, the case histories being selected from literally hundreds of virtually identical case histories.

In the treatment of multiple sclerosis, symptomatic relief provided according to the invention includes the improvement of bladder control through the relief of atonic conditions. The spasticity of muscles in the extremities is improved and alleviation of spastic bladder, nystagmus and poor balance is noted. Treatment according to the present invention typically increases stamina and endurance and provides the patient with an improved sense of wellbeing, an improved sensitivity to touch and an improvement of kidney function. Further, treatment according to the present invention enables some non-ambulatory patients to become ambulatory. Other patients report a lack of cold sensation in the extremities.

As with arthritis patients, a direct relationship exists between the local reaction to the injection at the injection site and the immediacy of favorable response.

The symptomatic improvement in spasticity (spastic bladder condition included), nystagmus, balance and the improved sense of well-being is believed attributable to the specific action of the post-synaptic "cobra" component of the present mixtures acting as a cell-specific blocking agent.

The krait component of the present mixtures is believed to have particular significance relative to the symptomatic improvement caused by the stimulation of a hypersensitive sensory nerve response as noted above. It is believed that the krait component of the present mixtures is responsible particularly for improved atonic bladder control, increase of the sensitivity of feeling in the extremities, and the improvement of strength and endurance. Treatment of patients diagnosed as having muscular distrophy has resulted in symptomatic improvement involving corrected incontinence, greater overall muscular strength and endurance and an improved sense of well-being.

Treatment of patients diagnosed as having Parkinson's disease has resulted in abatement of tremors. Patients diagnosed as having myasthenia gravis have shown reversed ptosis and greater strength and endurance.

Treatment according to the invention also produces dramatic improvement in herpes zoster, herpes simplex and lupus. In herpes simplex, a lack of subsequent reappearance has been noted in prone individuals. Further, a number of patients have noted the disappearance of moles and warts of certain types even though treatment for such condition was not intended.

Individuals treated according to the invention also exhibit a reduction of high blood pressure, an effect attributed to the presence of an anti-hypertensive component in the present mixtures. At least two diabetic patients being treated for multiple sclerosis have eliminated the need for insulin according to prescription of their personal physicians.

The following examples, which are representative of literally thousands of case histories, demonstrate the clinical efficacy of the present compositions of matter.

EXAMPLE 1

Patient diagnosed by neurologist and confirmed suffering from amyotrophic lateral sclerosis. A series of 22 injections of 0.1 cc of the mixture prepared as indicated above given over a 4 week period. Subjective condition stabilized and serum creatine phosphokinase (CPK) markedly increased at the onset of therapy with a definite trend toward normalization. Patient continues on therapy according to the invention with improved strength, decrease of fasciculations and general stabilization of condition.

The following examples are exemplary of literally hundreds of case histories involving treatment of patients under the care of licensed medical practitioners for the disease complex known as arthritis, and in a large percentage of the cases for rheumatoid arthritis. The following examples are exemplary of the large body of case history experience. The mixtures according to the invention utilized for treatment of these patients are essentially equivalent in strength and composition to the preferred mixture, the preparation of which is described above.

EXAMPLE 2

Female patient of 45 suffering from independently diagnosed rheumatoid arthritis since the age of 17. At initiation of treatment, severe pain was experienced, walking required the use of two canes, patient could not stand erect and could not perform useful work with the hands. Injections of 0.1 cc five times a week for four weeks resulted in noticeable improvement beginning after the first week. By the end of the treatment, patient could use hands normally and walk with high heeled shoes without assistance. General sense of well-being and subjective condition substantially improved.

EXAMPLE 3

Female, 86 years old, suffering from osteoarthritis for 20 years with condition progressively worsening. Cortisone occasionally used over 20 year period but aspirin most commonly used and used immediately prior to venom therapy. Initiation of therapy with 0.2 cc administered subcutaneously at 3–4 day intervals. After two weeks, patient reported substantial reduction in pain and discontinued aspirin. An additional two weeks of injection followed and was discontinued due to improved condition. Subjective condition remained constant for a three month period when pain began to return. Booster shots monthly again reduced pain.

EXAMPLE 4

Female, 87 years old, suffering from arthritis involving the knees which prevented walking. Substantial pain accompanies disability. Injection of 0.1 cc four times per week resulted after a two week period in substantial subjective relief of pain and increased mobility.

EXAMPLE 5

Female, 50 years old, diagnosed independently as suffering from rheumatoid arthritis involving the small joints of the hands and neck. Intradermal injections of 0.1 cc given at 3–5 day intervals initially and extended to 7–10 day intervals due to local reactions of the skin comprising wheal and erythema-type reactions. Subjective condition improved although some stiffness of the neck and a certain degree of pain, though lessened, remained.

EXAMPLE 6

Male, 69 years old, suffering from arthritis of the left shoulder and given 0.1 cc intradermally every third day. Improvement in mobility and reduction of pain noted after second injection. Condition has stabilized with continuing therapy without side effects.

EXAMPLE 7

Female, 68 years old, suffering from osteoarthritis. Injections of 0.1 cc intradermally given once weekly with marked improvement. Due to side effects including erythema of the forearm and edema of the full arm with erythema following an injection, subsequent injections were reduced to between 1/200 to 1/500 of a cc intradermally. Local reactions improved. Injections discontinued after stabilization of improved conditions. Subsequent courses of treatment initiated with lengthening periods between the courses as freedom from pain temporarily increases between courses of injections.

EXAMPLE 8

Female, 80 years old, suffering from arthritis involving the joints manifesting in severe pain and decreased mobility to include difficulty in walking. Over time, the patient had gradually become bedfast and able to become mobile for only short periods and then only with assistance. Intradermal injections of 0.1 cc were given at 3-5 day intervals. After the first injection, patient was able to walk unaided, to negotiate stairs and to walk outdoors for the first time in over a year. Subjective realization of pain in knees decreased. Continuing therapy stabilized condition to allow substantial increased mobility and decrease of pain in the joints.

EXAMPLE 9

Patient suffering from cervical myositis over a period of one year following injury sustained in an accident. Therapy comprising two injections of 0.1 cc intradermally over a period of a week caused pain to disappear. Therapy discontinued for over one year without recurrence of pain.

EXAMPLE 10

Patient suffering from tendonitis of the flexor tendonous of the right wrist, condition acute of approximately one week's duration. Two injections of 0.1 cc intradermally caused complete subsidance of symptomology.

EXAMPLE 11

Patient suffering from traumatic arthritis of cervical vertebrae and osteoarthritis of the lumbar vertebrae with chronic bursitis of the left shoulder and shortening of the tendons of the rotator cuff of the left shoulder. Prior attempts at therapy including previous cortisone and ultrasonic therapy were relatively unsuccessful. Patient complaining of pain and aching of the back and shoulder girdle. Marked improvement noted after injections at 3-day intervals comprised of 0.1 cc for the first two injections and 0.2 cc for the third injection. Marked improvement noted clinically in that the patient was able to move the arm in a greater circle without experiencing pain and has increased mobility of the neck. Neck capable of movement without prior instability and motion of the head lacked previous resistance which is typically experienced with Parkinson's disease on motion of a limb.

EXAMPLE 12

Patient suffering from generalized arthritis with marked involvement in the hips and lumbar sacral joints. Injections of 0.1 cc given intradermally at 3-day intervals. After four injections, subjective condition improved with reduced pain and increased mobility. Patient noted that condition of back was improved with reduced incidence of aches and pains and increased mobility. Dosage increased to 0.2 cc intradermally at 3-day intervals with continuing improvement.

EXAMPLE 13

Female, 88 years old, suffering from periodic occipital and post-cervical neuralgia for nearly 60 years and suffering from a present attack of 2 weeks duration. Injections increasing from 0.1 cc to 0.2 cc over a five day period (total of three injections) resulted in elimination of pain and no recurrence of symptomology over a two year period.

EXAMPLE 14

Male, 68 years old, suffering from interscapular myalgia and occipital neuralgia with attendant pain for two weeks. Injection at three day intervals of 0.1 cc for one week resulted in complete pain relief.

EXAMPLE 15

Male, 71 years old, suffering from tenosynovitis of the right shoulder for a three month period without relief from any treatment. A series of injections of 0.15 cc at 3-day intervals for a total of four injections with substantial reduction in pain noted after the second injection and continuing relief to a stable condition after four injections.

EXAMPLE 16

Female, 68 years old, severe right supraorbital neuralgia of two week duration. A series of 0.15-0.2 cc injections at 3-day intervals over a one week period followed by monthly injections eliminated pain by the end of the fourth month. No recurrence after one year.

EXAMPLE 17

Female, 46 years old, suffering from chronic arthritis with deformation of finger joints. Daily injections for 2 weeks, injections every other day for one month, twice weekly injections for one month followed by weekly injections for one month, dosages being varied from 0.1 cc to 0.2 cc over the period of injections. Patient reported discontinuance of pain, increased use of joints, deposits clinically noted as being reduced.

EXAMPLE 18

Female, 69 years old, suffering from independently diagnosed rheumatoid arthritis with attendant pain and decreased mobility. Injections of 0.1 cc at 3-day intervals for a total of ten treatments resulting in reduction of pain and increased mobility.

The following examples constitute only a representative fraction of literally thousands of case histories involving the treatment of multiple sclerosis under the direction of licensed medical practitioners in situations where the condition was independently diagnosed. The composition utilized in the following treatments have primarily consisted of the particularly preferred composition described by preparation above.

EXAMPLE 19

Patient, CD, suffering from multiple sclerosis and confined to a wheelchair, incontinent, impaired sense of balance, blurred vision and numbness in extremities and torso. Daily injections subcutaneously of 0.1 cc on a continuing basis resulted in improved memory retention, improved speech and vision, improved balance and increased sensory perception. Patient is now able to walk unaided for short periods of time. Therapy continuing.

EXAMPLE 20

Patient, BD, independently diagnosed as having multiple sclerosis. Classical symptomology. Daily injections beginning with 0.1 cc and increasing gradually to 0.3 cc at the present time has provided substantial improvement subjectively, increased bladder control and increased stamina. Therapy continuing.

EXAMPLE 21

Patient, C.C., diagnosed as having multiple sclerosis with numbness in feet, reduced energy level, poor bladder control and reduced coordination. Daily injections of 0.1 cc for four week period has resulted in relief of numbness, increased energy and sense of well-being, improved bladder control and improved ability to write, walk and other activities requiring coordination. After one month of treatment, patient has been in remission for over one year.

EXAMPLE 22

Patient, CB, diagnosed as multiple sclerosis with therapy of 0.1 cc administered five times weekly. After one week, leg brace needed to control "toe drop" no longer needed and improved degree of bladder control restored sufficient to allow natural warning to enable normal bladder relief. Present therapy of three shots weekly necessary to prevent recurrence of bladder incontinence and other symptomology.

EXAMPLE 23

Patient, ED, diagnosed as having multiple sclerosis for 12 years. Gradual progression of disease caused deterioration of use of both legs and right arm and hand; bladder and bowel disabilities developed along with diminished eyesight and hearing. Severe emotional problems. Legs painful, aching and cold with occasional strong spasms. Patient exhibited little endurance and fatigued easily. Daily injections initially at 0.1 cc and increasing to 0.5 cc over a one month period resulted in a return to normal bladder and bowel function, substantial improvement in eyesight including the return of night vision, substantial hearing improvement. Patient's emotional stability has returned and an increase in strength and endurance allows walking for short periods. Legs no longer cold; improved circulation experienced. Patient exhibits less fatigue and has a substantially increased sense of well-being along with much improved comfort.

EXAMPLE 24

Patient, SG, diagnosed as multiple sclerosis. Injections of 0.1 cc initially increasing gradually to 0.3 cc over a six month period, injections being given daily for the first month and three times weekly since the first month. General condition improved.

EXAMPLE 25

Patient, JD, suffering from independently diagnosed multiple sclerosis with symptomology including poor walking gait, lack of feeling in fingers, occasional double vision, lost color perception, poor bladder control, inability to sleep, rapid fatigue, occasional slurred speech and reduced coordination manifested in inability to write legibly. After daily injections of 0.1 cc for one week, sensitivity returned to feet, speech improved, and improved muscular control. After four weeks of daily injections gradually increased to 0.2 cc, patient exhibited ability to walk for increasingly long periods of time without holding onto walls. Emotional condition substantially improved.

EXAMPLE 26

Patient, SK, suffering from multiple sclerosis with symptomology including coordination loss, spasticity in the legs, occasional loss of bladder control, extreme fatigue and severe depression. Injections initially at 0.1 cc daily and increasing after one month to 0.5 cc three times weekly has resulted in increased bladder control, increased mobility, increased coordination and balance, and a substantial increase in energy level and emotional well-being.

EXAMPLE 27

Patient, ND, diagnosed with multiple sclerosis. Injections beginning at 0.1 cc daily and increasing to 0.3 cc daily resulted in improved bladder control and improved vision. Shrinkage of calf muscles in right leg prior to treatment arrested and general increase of peripheral neurological sensitivity throughout body. Therapy continuing.

EXAMPLE 28

Patient, RK, diagnosed as having multiple sclerosis for two years prior to initiation of therapy although symptomology began ten years prior to diagnosis. Symptomology includes dropped right foot, reduced feeling in right foot and right hand, poor balance and coordination, insomnia, constant fatigue, pain and aches in both legs along with spastic condition, poor bladder and bowel retention, slurred speech, blurred and double vision, and severe headaches. Injections of 0.15 cc daily resulted in improvement in condition after less than one week. After two weeks of daily injections, walking gait substantially improved, bladder and bowel control improved, normal speech returned, increased energy and strength levels, vision improved, improved vitality and sense of well-being. Some symptomology, such as the dropped right foot, not improved appreciably.

EXAMPLE 29

Patient, NL, diagnosed as multiple sclerosis twelve years prior to initiation of treatment. Symptomology including necessity for use of a cane, dropped left foot, reduced stamina and endurance. Daily injections of 0.1 cc after seven days resulted in increase in strength level, improved ability to move the legs. Daily injections for nine months has resulted in increasing improvement including ability to walk without assistance, ability to stand up in order to allow dressing, ability to handle household work chores and shop, including the ability to remain standing for more than 30 minutes at a time. Patient now has sufficient mobility to negotiate stairs and to return to work.

EXAMPLE 30

Patient, DS, diagnosed as multiple sclerosis with symptomology of stiff left leg and inability to walk for moderate distances only with a walker and requiring the use of a wheelchair for relatively long distances. Energy level reduced with constant shortness of breath and muscle spasms. After fourth injection of 0.1 cc over a four day period, walking gait improved noticeably with continuing improvement until patient gained ability to walk normally after one month of daily injections. Energy level again increasing after the first week of injections; shortness of breath and muscle spasms discontinued. Maintenance of daily dosage of 0.2 cc has continued after one year to alleviate symptomology.

EXAMPLE 31

Patient, MH, diagnosed as multiple sclerosis. After five daily shots of 0.1 cc, bladder control improved substantially and vision improved. After 18 daily shots, digestion improved and spastic colon substantially improved. Continuing therapy of four injections of 0.2 cc four times weekly have retained above-noted benefits and increased level of strength and endurance.

EXAMPLE 32

Patient, OM, diagnosed with multiple sclerosis and unable to stand, walk or write. Balance and bladder control severely impaired. Therapy including daily injections of 0.1 cc for one month with increasing dosages to 0.4 cc three times weekly has resulted in increased coordination, the ability to stand stationarily for a time sufficient to shower, the ability to walk within the home without a cane or other support, an improved sense of balance, and complete return of bladder control.

EXAMPLE 33

Patient, BF, diagnosed with multiple sclerosis with symptomology including severe nystagmus, dysplexia, vertigo, insomnia, bilateral gait, fatigue, loss of balance, and severe pain. Therapy comprising daily injections of 0.1 cc increasing to 0.5 cc for two months have eliminated the pain and improved the gait, improved balance and increased endurance. Nystagmus eliminated and sense of well-being increased.

EXAMPLE 34

Patient, PT, diagnosed with multiple sclerosis and treated with daily injections of 0.1 cc with return of full bladder and bowel control and increased energy level. Continuing therapy involving four injections weekly of 0.2 cc.

In order to avoid prolixity in the presentation of case histories, it is to be understood that more than 2000 additional case histories exist which relate to improvement of patient condition through the injection of disease mitigating quantities of the present mixtures to patients suffering from amyotropic lateral sclerosis, multiple sclerosis, muscular distrophy, Parkinson's disease and other degenerative disorders. The quantities of the present mixtures injected have varied within a substantial range with more than 1.0 cc being injected daily after a gradual increase from approximately 0.1 cc or less (depending upon initial sensitivity) at the beginning of treatment. Dozens of case histories also exist relative to the treatment of herpes zoster, herpes simplex, herpes genitalis, lupus and other conditions such as are described hereinabove. Two multiple sclerosis patients treated according to the invention and who also were suffering from diabetes were taken off insulin therapy by their physicians due to a reported lack of need therefor. Substitution of varying venom sources for the cobra, krait, and viper components of the venom have been accomplished with similar results. In particular, substitution of the viper component with any of the crotalid venoms results in favorable treatment capabilities.

The component or components of the present composition which stimulate the immune mechanism of the body should also be understood to comprise isolation of the venom component known as nerve growth factor, this component being present in viperid venoms in greatest quantity. The present composition of matter may also be preserved with conventional preservative other than that preservative mentioned above. When use of the composition of matter is to be essentially immediate, use of a perspective is not necessary. Although it is believed to be apparent from the foregoing, it is also to be understood that the present compositions of matter are useful in the practice of veterinary medicine, such as in the treatment of canine arthritis.

The foregoing is considered to be illustrative of the scope and the effectiveness of the invention. However, it is to be understood, that within the scope of the invention as indicated herein, the invention can be practiced other than as explicitly described hereinabove without departing from the intended scope of the invention.

What is claimed is:

1. A composition of matter having pharmacological activity comprising in an administerable form at least one post-synaptic neurotoxin, at least one pre-synaptic neurotoxin, and at least one component capable of stimulating the immune mechanisms of the body.

2. The composition of matter of claim 1 wherein the post-synaptic neurotoxin comprises the α-toxin obtained from the venom of an elapid snake selected from a species of the genera Naja, Ophiophagus or Dendroaspis, the pre-synaptic neurotoxin comprises β-bungarotoxin obtained from the venom of the elapid snakes *Bungarus multicinctus,* and the component capable of stimulating the immune mechanisms of the body at least comprises a venom obtained from a vipered snake.

3. The composition of matter of claim 2 wherein the viperid venom comprises a venom of the Family Vipera, subfamily Crotalinae.

4. A composition of matter having pharmacological activity and having therapeutic benefits in the treatment of the symptomology of progressive degenerative neurological diseases, the disease complex known as arthritis, viral infections and autoimmune disorders, comprising in an administrable form effective amounts of a post-synaptic neurotoxin obtained from the venom of an elapid snake, a pre-synaptic neurotoxin obtained from the venom of an elapid snake, and the venom obtained from a viperid snake.

5. The composition of matter of claim 4 wherein the post-synaptic neurotoxin is obtained from the venom of an elapid snake selected from a species of the genera Naja, Ophiophagus, or Dendroaspis.

6. The composition of matter of claim 5 wherein the genera further includes Hemachatus and the genera of the family Hydrophiidae.

7. The composition of matter of claim 4 wherein the post-synaptic neurotoxin is obtained from the venom of *Naja naja siamensis* (kaouthia).

8. The composition of matter of claim 7 wherein the post-synaptic neurotoxin comprises the α-toxin.

9. The composition of matter of claim 4 wherein the pre-synaptic neurotoxin is obtained from the venom of an elapid snake selected from a species of the genera Bungarus, Oxyuranus, or Notechis.

10. The composition of matter of claim 4 wherein the pre-synaptic neurotoxin is selected from the group consisting of β-bungarotoxin and *Bungarus multicinctus*, Crotoxin from *Crotalus durissus terrificus*, Notexin from *Notechis scutatus*, and Taipoxin from *Oxyuranus scutalatus*.

11. The composition of matter of claim 4 wherein the viperid venom comprises a venom of the Family Vipera, subfamily Crotalinae.

12. The composition of matter of claim 11 wherein the viperid venom comprises *Agkistrodon piscivorus*.

13. The composition of matter of claim 4 wherein the post-synaptic neurotoxin comprises α-toxin isolated from *Naja naja siamensis* (kaouthia), the pre-synaptic neurotoxin comprises β-bungarotoxin isolated from *Bungarus multicinctus*, and the viperid venom comprises venom extracted from *Agkistrodon piscivorus*.

14. The composition of matter of claim 13 wherein the viperid venom is present in the mixture in a quantity ten times greater than either of the remaining components of the mixture.

15. The composition of matter of claim 13 wherein the post-synaptic and pre-synaptic neurotoxins are present in a ratio of 0.176 grams to 8.8 liters of total saline solution and the viperid venom is present in a ratio of 1.76 grams to 8.8 liters of total solution.

16. The compositions of matter of claim 15 wherein the solution is stabilized with an effective amount of Thimerosal.

17. The method of claim 16 wherein the mammal treated comprises man.

18. A method of treatment of mammals suffering from progressive degenerative neurological disease comprising administering to the mammal a disease mitigating amount of a mixture comprised of at least one post-synaptic neurotoxin, at least one pre-synaptic neurotoxin, and at least one component capable of stimulating the immune mechanism thereof.

19. The method of claim 18 wherein the post-synaptic neurotoxin comprises α-toxin isolated from *Naja naja siamensis* (kaouthia) the pre-synaptic neurotoxin comprises β-bungarotoxin isolated from *Bungarus multicinctus*, and the last-mentioned component comprises a crotalid snake venom.

20. The method of claim 19 wherein the crotalid snake venom comprises venom extracted from *Agkistrodon piscivorus*.

21. The method of claim 20 wherein the dosage administered daily over an extended period of time is in the range of 0.05 cc to 1.5 cc, the dosage being taken from a solution wherein the post-synaptic and presynaptic neurotoxins are present in a ratio of 0.176 grams each and the crotalid venom is present in a ratio of 1.76 grams to 8.8 liters of normal saline solution.

22. A method of treatment of mammals suffering from the disease complex referred to as arthritis including rheumatoid arthritis comprising administering to the mammal a disease mitigating amount of a mixture comprised of at least one post-synaptic neurotoxin, at least one presynaptic neurotoxin, and a venom from a viperid snake.

23. The method of claim 22 wherein the post-synaptic neurotoxin comprises α-toxin isolated from Naja naja siamensis (kaouthia), the pre-synaptic neurotoxin comprises β-bungarotoxin isolated from *Bungarus multicinctus*, and the viperid venom is extracted from a crotalid snake.

24. The method of claim 23 wherein the crotalid snake comprises *Agkistrodon piscivorus*.

25. The method of claim 22 wherein the mammal treated comprises man.

26. A method of treatment of mammals suffering from viral infections including herpes zoster, herpes genitalis and herpes simplex, autoimmune disorders, and hypertension, comprising administering to the mammal a disease mitigating amount of a mixture comprised of at least one post-synaptic neurotoxin, at least one presynaptic neurotoxin, and a venom from a viperid snake.

27. The method of claim 26 wherein the post-synaptic neurotoxin comprises an α-toxin isolated from *Naja naja siamensis* (kaouthia), the pre-synaptic neurotoxin comprises β-bungarotoxin isolated from *Bungarus multicinctus*, and the viperid venom is extracted from a crotalid snake.

28. The method of claim 26 wherein the mammal treated comprises man.

29. A composition of matter having pharmacological activity comprising in an administrable form at least one post-synaptic neurotoxin obtained from the venom of an elapid snake, a pre-synaptic neurotoxin obtained from the venom of an elapid snake, and a venom obtained from a viperid snake.

30. The composition of matter of claim 29 wherein the post-synaptic neurotoxin is obtained from the venom of an elapid snake selected from a species of the genera Naja, Ophiophagus, or Dendroaspis.

31. The composition of matter of claim 29 wherein the post-synaptic neurotoxin is obtained from the venom of Naja naja siamensis (kaouthia).

32. The composition of matter of claim 31 wherein the post-synaptic neurotoxin comprises the α-toxin.

33. The composition of matter of claim 29 wherein the pre-synaptic neurotoxin is obtained from the venom of an elapid snake selected from a species of the genera Bungarus, Oxyuranus, or Notechis.

34. The composition of matter of claim 29 wherein the pre-synaptic neurotoxin is selected from the group consisting of β-bungarotoxin from *Bungarus multicinctus*Crotoxin from *Crotalus durissus terrificus*, Notexin from *Notechis scutatus*, and Taipoxin from *Oxyuranus scutalatus*.

35. The composition of matter of claim 29 wherein the viperid venom comprises a venom of the Family Vipera, subfamily Crotalinae.

36. The composition of matter of claim 29 wherein the viperid venom comprises *Agkistrodon piscivorus*.

37. The composition of matter of claim 29 wherein the post-synaptic neurotoxin comprises α-toxin isolated from Naja naja siamensis (kaouthia), the pre-synaptic neurotoxin comprises β-bungarotoxin isolated from *Bungarus multicinctus*, and the viperid venom comprises venom extracted from *Agkistrodon piscivorus*.

38. The composition of matter of claim 37 wherein the viperid venom is present in the mixture in a quantity ten times greater than either of the remaining components of the mixture.

39. The composition of claim 37 wherein the post-synaptic and pre-synaptic neurotoxins are present in a ratio of 0.176 grams each to 8.8 liters of total saline solution and the viperid venom is present in a ratio of 1.76 grams to 8.8 liters of total solution.

40. The composition of matter of claim 39 wherein the solution is stabilized with an effective amount of Thimerosal.

* * * * *